(12) United States Patent
Pischel et al.

(10) Patent No.: US 10,061,354 B2
(45) Date of Patent: Aug. 28, 2018

(54) DOCKING STATION FOR ELECTRONIC DEVICE

(71) Applicant: Gamber-Johnson LLC, Stevens Point, WI (US)

(72) Inventors: Travis Pischel, Marshfield, WI (US); Jason Lewandowski, Stevens Point, WI (US)

(73) Assignee: Gamber-Johnson LLC, Stevens Point, WI (US)

(*) Notice: Subject to any disclaimer, the term of this patent is extended or adjusted under 35 U.S.C. 154(b) by 0 days.

(21) Appl. No.: 15/724,184

(22) Filed: Oct. 3, 2017

(65) Prior Publication Data

US 2018/0107248 A1 Apr. 19, 2018

Related U.S. Application Data

(60) Provisional application No. 62/408,398, filed on Oct. 14, 2016.

(51) Int. Cl.
*G06F 1/16* (2006.01)
*H05K 5/02* (2006.01)
*B60R 11/02* (2006.01)

(52) U.S. Cl.
CPC ......... *G06F 1/1632* (2013.01); *H05K 5/0221* (2013.01); *A61B 2560/0456* (2013.01); *B60R 11/0252* (2013.01)

(58) Field of Classification Search
CPC . G06F 1/1632; H05K 5/0221; B60R 11/0252; A61B 2560/0456
See application file for complete search history.

(56) References Cited

U.S. PATENT DOCUMENTS

| 5,633,782 A | 5/1997 | Goodman et al. |
| 5,751,546 A | 5/1998 | Clark et al. |
| 5,790,375 A | 8/1998 | Lee |

(Continued)

FOREIGN PATENT DOCUMENTS

WO 2010018011 2/2010

OTHER PUBLICATIONS

Extended European Patent Office Search Report for Application No. 17195820.0 dated Feb. 15, 2018, 7 pages.

(Continued)

*Primary Examiner* — Dimary Lopez Cruz
*Assistant Examiner* — Abhishek Rathod
(74) *Attorney, Agent, or Firm* — Michael Best & Friedrich LLP

(57) ABSTRACT

A docking station for a portable electronic device includes a cradle portion for supporting a first edge of the portable electronic device, a body portion extending away from the cradle portion, and a latching portion coupled to the body portion for securing a second edge of the portable electronic device when the portable electronic device is supported in the docking station. The latching portion includes a first latch movable relative to the body portion between a latched position and an unlatched position, a second latch spaced from the first latch and movable relative to the body portion between a latched position and an unlatched position, and a control bar coupled to each of the first and second latches such that movement of the control bar by a user simultaneously moves both the first and second latches to the unlatched positions.

21 Claims, 15 Drawing Sheets

(56) References Cited

U.S. PATENT DOCUMENTS

| | | |
|---|---|---|
| 5,867,774 A | 2/1999 | Summers et al. |
| 6,042,414 A | 3/2000 | Kunert |
| 6,053,759 A | 4/2000 | Kunert |
| 6,069,790 A | 5/2000 | Howell et al. |
| 6,101,087 A | 8/2000 | Sutton et al. |
| 6,119,184 A | 9/2000 | Takahama |
| 6,229,893 B1 | 5/2001 | Chen |
| 6,264,488 B1 | 7/2001 | Helot et al. |
| 6,520,466 B1 | 2/2003 | Blanchard, III et al. |
| 6,532,152 B1 | 3/2003 | White et al. |
| 6,549,416 B2 | 4/2003 | Sterner et al. |
| 6,585,212 B2 | 7/2003 | Carnevali |
| 6,647,248 B1 | 11/2003 | Ortscheid et al. |
| 6,785,567 B2 | 8/2004 | Kato |
| 7,017,243 B2 | 3/2006 | Carnevali |
| 7,052,296 B2 | 5/2006 | Yang et al. |
| 7,180,753 B2 | 2/2007 | Kerrigan et al. |
| 7,273,203 B2 | 9/2007 | Carnevali |
| 7,274,564 B2 | 9/2007 | Rossini |
| D585,897 S | 2/2009 | Carnevali |
| 7,911,779 B1 | 3/2011 | Tarnoff |
| 8,179,672 B2 | 5/2012 | Carnevali |
| 8,182,426 B2 | 5/2012 | Zhao et al. |
| 8,315,048 B2 | 11/2012 | Tarnoff |
| 9,535,457 B1 * | 1/2017 | Vier .................. G06F 1/1632 |
| 9,612,616 B2 | 4/2017 | Tarnoff |
| 9,898,041 B2 * | 2/2018 | Blowers ................ F16M 13/00 |
| 2003/0083115 A1 | 5/2003 | Kato |
| 2003/0174855 A1 | 9/2003 | Hawkins et al. |
| 2007/0127204 A1 | 6/2007 | Muenzer et al. |
| 2007/0190843 A1 | 8/2007 | Snow et al. |
| 2008/0078071 A1 | 4/2008 | Gong |
| 2008/0239658 A1 | 10/2008 | Chou et al. |
| 2008/0270664 A1 | 10/2008 | Carnevali |
| 2009/0045234 A1 | 2/2009 | Carnevali |
| 2009/0140113 A1 | 6/2009 | Carnevali |
| 2009/0179435 A1 | 7/2009 | Lev et al. |
| 2009/0201636 A1 | 8/2009 | Doherty et al. |
| 2009/0213536 A1 | 8/2009 | Lewandowski et al. |
| 2011/0095159 A1 | 4/2011 | Carnevali |
| 2011/0266230 A1 | 11/2011 | Carnevali |
| 2012/0045931 A1 | 2/2012 | Carnevali |
| 2012/0045932 A1 | 2/2012 | Carnevali |
| 2013/0050932 A1 | 2/2013 | Williams |
| 2017/0199545 A1 | 7/2017 | Tarnoff |

OTHER PUBLICATIONS

Gamber Johnson, Dell D600/D610 Docking Cradles, features sheet, undated, 1 page.

RAM Mounts, UNPKD Passive RAM Cradle Motion C5, part details webpage, printed Aug. 24, 2009 from http://www.ram-mount.com/CatalogResults/PartDetails/tabid/63/partid/082065077045072 . . . , 1 page.

RAM Mounts, RAM Mount for Motion C5, part details webpage, printed Jul. 29, 2009 from http://www.ram-mount.com/CatalogResults/PartDetails/tabid/63/partid/082065077045049 . . . , 1 page.

RAM Mounts, RAM Dbl Suction Mount for Motion C5, part details webpage, printed Jul. 29, 2009 from http://www.ram-mount.com/CatalogResults/PartDetails/tabid/63/partid/082065077045049 . . . , 1 page.

RAM Mounts, RAM Aircraft Seat Rail Sys Motion LS800, part details webpage, printed Jul. 29, 2009 from http://www.ram-mount.com/CatalogResults/PartDetails/tabid/63/partid/082065077045049 . . . , 1 page.

RAM Mounts, RAM Mounts for The Panasonic Toughbook CF-H1, product webpages, undated, 2 pages.

Rugged PC review.com, RAM Mounts for Panasonic Toughbook CF-H1, product webpages, undated, 2 pages.

Rugged PC review.com, Panasonic Toughbook H1, product webpages, undated, 11 pages.

Havis Inc., "Owner's Manual Havis Docking Station for Dell Latitude Rugged 12 Tablet," DS-DELL-600-SERIES_OMN_5-17, publication date unknown, publicly available at least as early as Jun. 1, 2018, (12 pages).

Havis Inc., "Havis DS-DELL-600 Series Docking Station," OEM Off-Highway, <https://www.oemoffhighway.com/operator-cab/operator-interface/monitors-display/operator-interface/product/12131713/havis-inc-havis-dsdell600-series-docking-station> webpage available at least as early as Oct. 28, 2015, (11 pages, Statement of Relevance included).

Havis Inc., "Havis Partners With Dell to Offer New DS-DELL-600 Series Docking Station for the Dell Latitude 12 Rugged Tablet," Havis Press Releases, <http://customers.havis.com/index.php/press-releases/item/951-havis-partners-with-dell-for-latitude-12-rugged-tablet-docking-station> webpage available at least as early as Oct. 28, 2015, (1 page).

* cited by examiner

DOCKING STATION FOR ELECTRONIC DEVICE

RELATED APPLICATIONS

This application claims priority to U.S. Provisional Application No. 62/408,398 filed Oct. 14, 2016, the entire content of which is hereby incorporated by reference herein.

BACKGROUND

The present invention relates to docking stations for electronic devices, and more specifically to docking stations for tablet computers.

SUMMARY

In one embodiment, the invention provides a docking station for a portable electronic device. The docking station includes a cradle portion for supporting a first edge of the portable electronic device, a body portion extending away from the cradle portion, and a latching portion coupled to the body portion for securing a second edge of the portable electronic device when the portable electronic device is supported in the docking station. The latching portion includes a first latch movable relative to the body portion between a latched position and an unlatched position, a second latch spaced from the first latch and movable relative to the body portion between a latched position and an unlatched position, and a control bar coupled to each of the first and second latches such that movement of the control bar by a user simultaneously moves both the first and second latches to the unlatched positions.

In one aspect, each of the first and second latches is pivotally coupled to a housing at a respective pivot point, and the first and second latches both rotate in the same direction about their respective pivot points between the latched and unlatched positions.

In another aspect, the control bar is coupled to the first latch at a first pivot point, and the control bar is coupled to the second latch at a second pivot point. A distance between the first and second pivot points is constant during movement of the first and second latches between the latched and unlatched positions.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. As used herein and in the appended claims, terms such as "upwardly," "downwardly," "front," "rear," "upper" and "lower" are used only to help describe the illustrated embodiment. These and other directional terms are not intended to be limiting of the described and illustrated embodiment.

Figure 20:
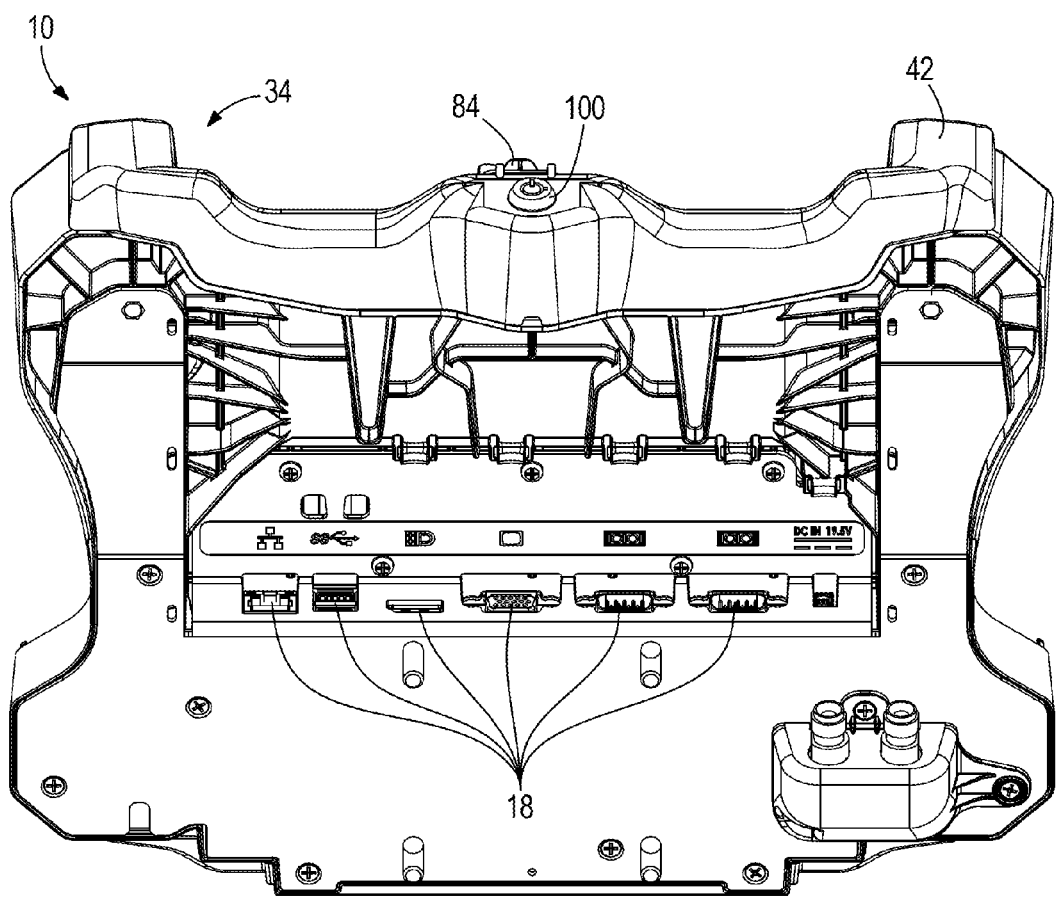
FIG. 20 is a rear view of the docking station of FIG. 1.

FIGS. 1-19 illustrate a docking station 10 for a portable electronic device 14. In the illustrated embodiment, the portable electronic device 14 is a Dell® tablet computer, however, in other embodiments, different portable electronic devices may be used with the docking station 10. The docking station 10 is sized and configured to receive and securely hold the portable electronic device 14. In the illustrated embodiment, an electrical connector 16 and RF connectors 17 (see FIG. 17) of the docking station 10 electrically connect the portable electronic device 14 to the docking station 10. Input/output connectors 18 for power and/or data are provided along a lower portion of the front of the docking station 10 (see FIGS. 1 and 8) as well as on a rear of the docking station 10 (see FIG. 20). The docking station 10 includes a cradle portion 22 that receives and supports a lower edge 26 of the portable electronic device 14. A body portion 30 of the docking station 10 extends away from the cradle portion 22 toward a latching portion 34 that is configured to engage and secure an upper edge 38 of the portable electronic device 14 in the docking station 10.

Figure 3:
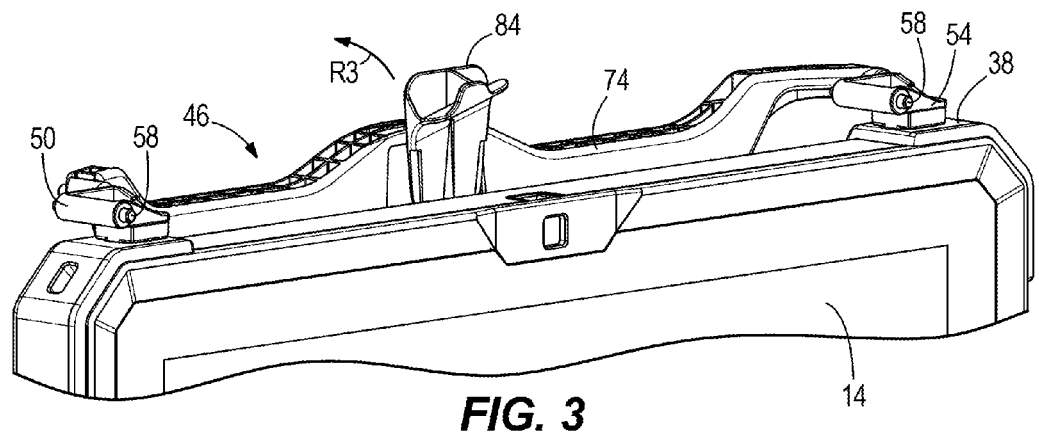
FIG. 3 is a perspective view of a latching system incorporated in the docking station of FIG. 2, illustrated with the remaining structure of the docking station removed for clarity.
Figure 4:
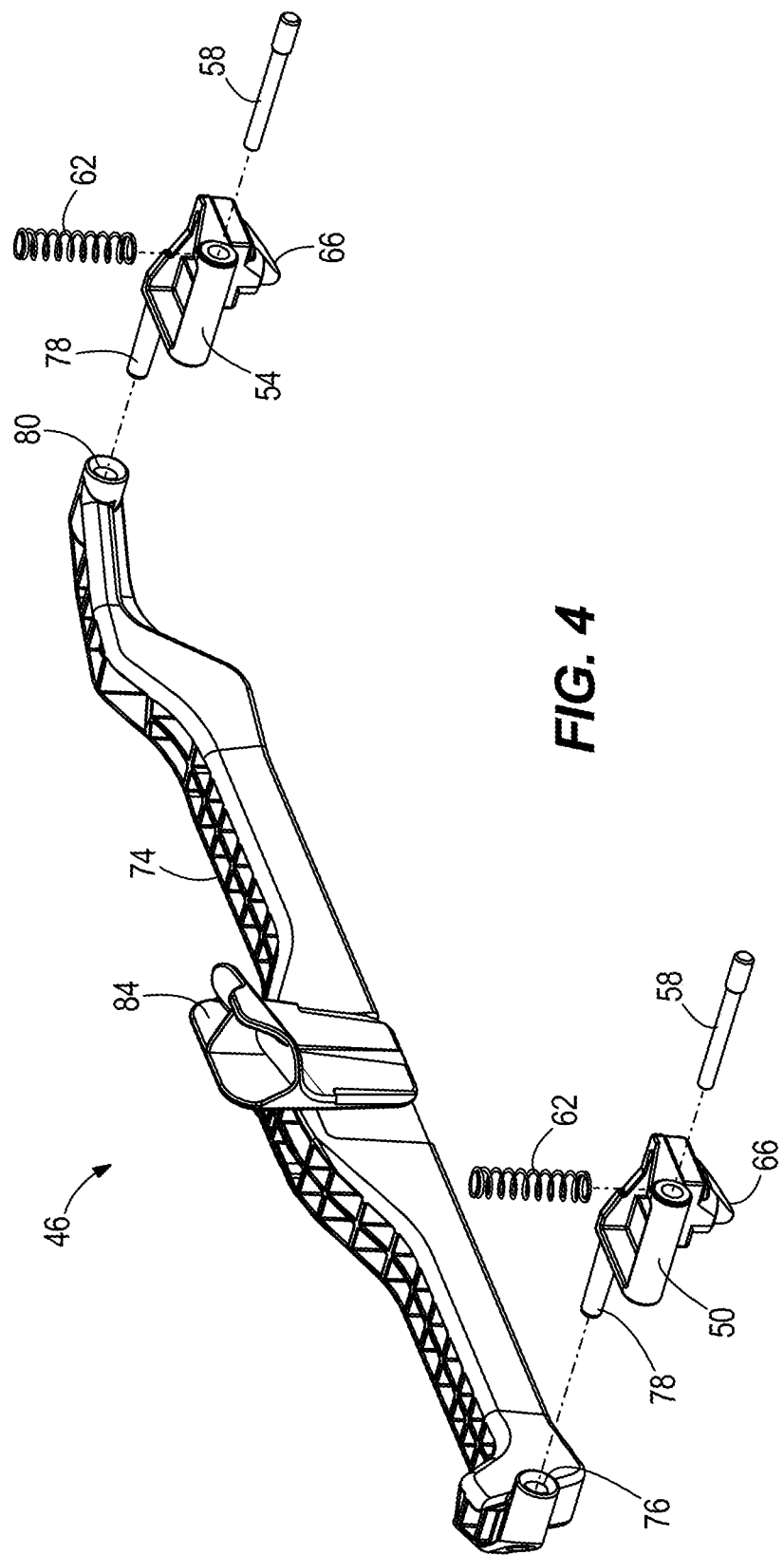
FIG. 4 is an exploded view of the latching system shown in FIG. 3.
Figure 5:
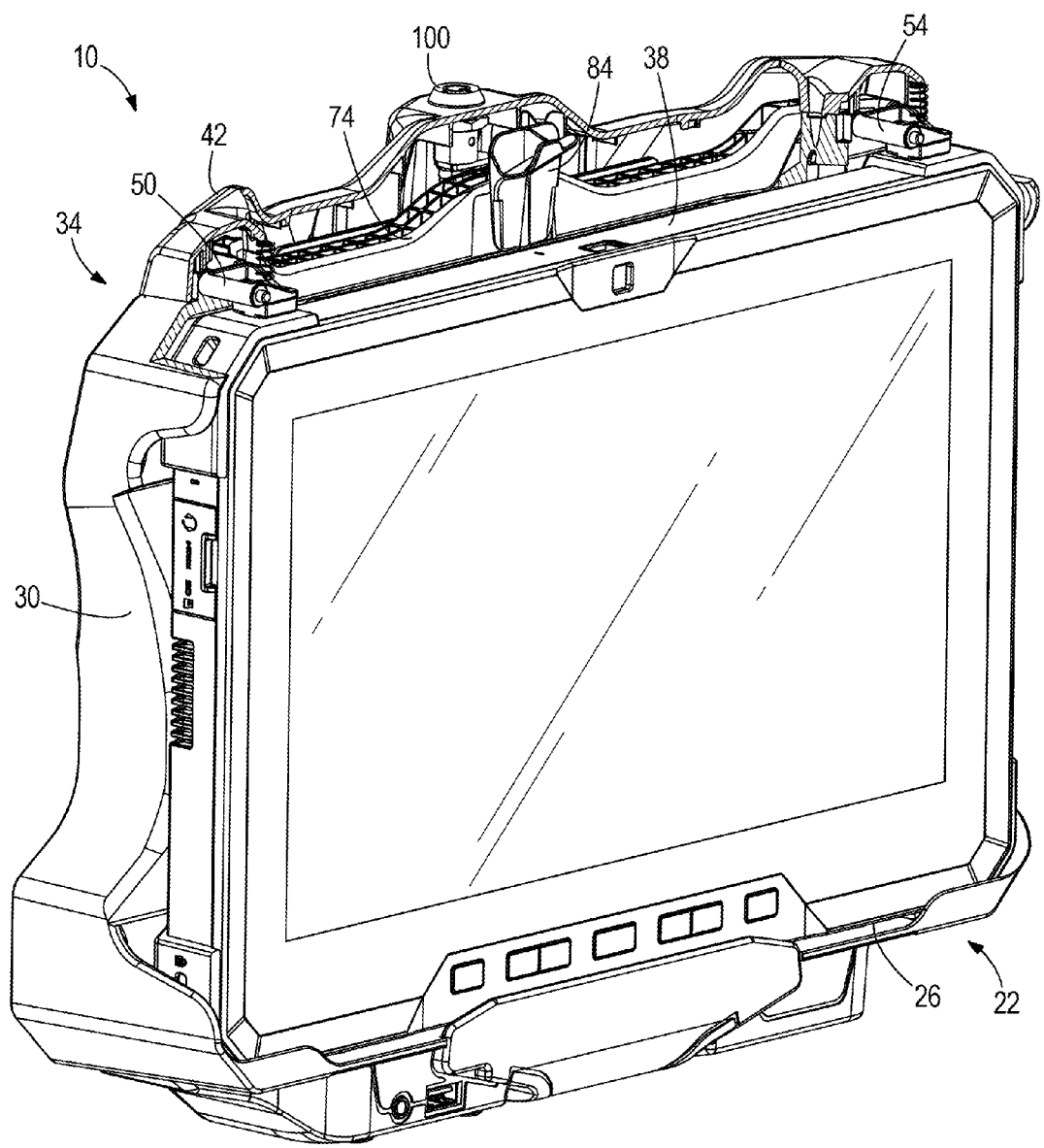
FIG. 5 is a perspective view of the docking station, partially broken away, illustrating the latching system in the latched position retaining the electronic device.
Figure 6:
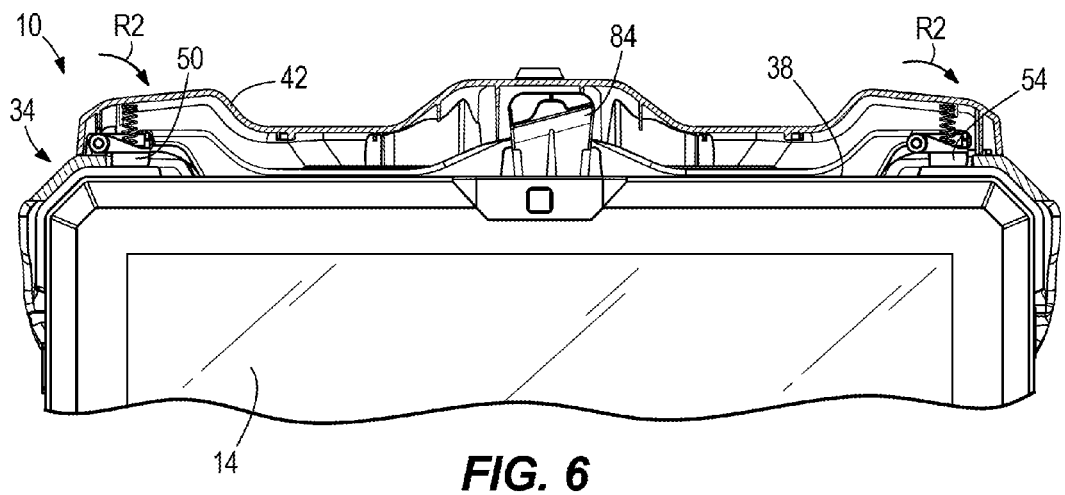
FIG. 6 is a partial front view of FIG. 5 illustrating the latching system in the latched position retaining the electronic device.
Figure 7:
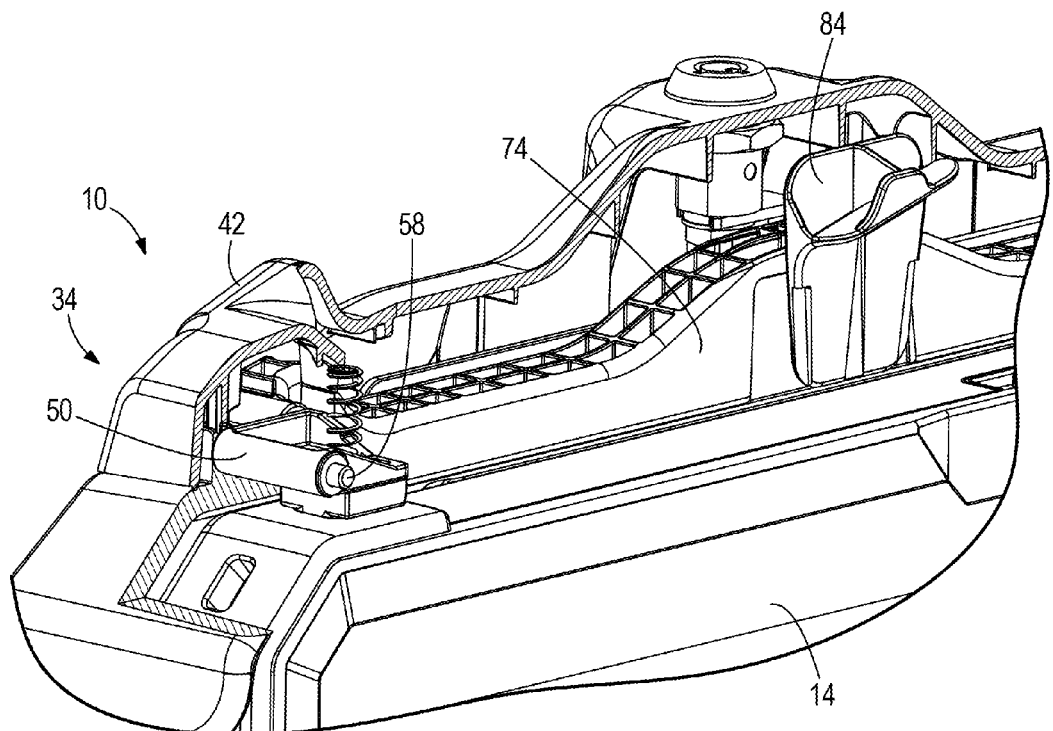
FIG. 7 is an enlarged partial perspective view of the arrangement of FIG. 5.

The latching portion 34 of the docking station 10 includes the plastic housing 42 of the docking station 10 adjacent the upper edge 38 of the portable electronic device 14, as well as a latching system 46 (see FIGS. 3 and 4) that cooperates with and is movable relative to the housing 42 and the body portion 30 to selectively latch and unlatch the portable electronic device 14 from the docked state within the docking station 10. FIGS. 3 and 4 illustrate the components of latching system 46 with the housing 42 removed for clarity. The latching system 46 includes first and second latches 50, 54, which in the illustrated embodiment are injection molded plastic, are identical to one another, and are spaced apart from one another to be positioned generally adjacent the opposite upper corners of the latching portion 34 of the docking station 10 (and therefore adjacent the opposite upper corners of the portable electronic device 14). Each latch 50, 54 is pivotally connected to the housing 42 via a pivot pin 58 that fixes the latches 50, 54 to the housing 42 while permitting rotational movement of the latches 50, 54 about an axis defined by the pin 58.

A spring 62 (see FIG. 4) associated with each latch 50, 54 biases the latches 50, 54 toward a latched position (see FIGS. 5-7 and 14), in which a distal portion 66 (see FIGS. 4 and 15A) of each latch 50, 54 is received in a corresponding aperture 70 (see FIGS. 11-14) formed in the upper edge 38 of the portable electronic device 14 to secure the portable electronic device 14 in the docked state. The spring bias can be overcome to allow the latches 50, 54 to move to an unlatched position (see FIGS. 8-10) in which the distal portions 66 of each latch 50, 54 are removed from within the apertures 70, allowing the portable electronic device 14 to be removed from the docking station 10. The springs 62 in the illustrated embodiment are compression springs that have one free end seated on a boss or seat (not shown) on an in inner surface of the housing 42 and another free end seated on a boss or seat 72 (see FIG. 15B) within a hollow interior portion of the latch 50, 54 to urge the latches 50, 54 downwardly and away from the inner surface of the housing 42. In other embodiments, the springs 62 could be torsion springs supported on or about the pivot pins 58.

With reference to FIG. 4, the latching system 46 further includes an elongated control bar 74 interconnecting the latches 50, 54. A first aperture 76 formed in a first end of the control bar 74 receives a projection or pin 78 connected to the first latch 50 to pivotally couple the control bar 74 to the first latch 50 at a first pivot point. The illustrated pin 78 is integrally formed as a single piece with the first latch 50. In a similar manner, a second aperture 80 formed in a second end of the control bar 74 receives a projection or pin 78 connected to the second latch 54 to pivotally couple the control bar 74 to the second latch 54 at a second pivot point. The pins 78 extend from the first and second latches 50, 54 at locations spaced from the pivot pins 58 such that movement of the control bar 74 in an upward direction will provide an upward force (via the pins 78 received in the apertures 76, 80) on the latches 50, 54 to rotate the latches 50, 54 to the unlatched position. In other embodiments, the pins 78 could be integrally formed with the control bar 74 to be received in apertures formed in the latches 50, 54. Alternatively, the pins 78 could be separate parts received in apertures formed in both the control bar and the latches. In yet another alternative embodiment, the two springs 62 that interact with the latches 50, 54 could be replaced with one or more tension or compression springs that would act directly on the control bar 74 to bias the control bar 74 toward the downward position. The illustrated control bar 74 is a rigid, one-piece member made of molded plastic such that movement of the control bar 74 upwardly will move both latches 50, 54 to the unlatched position simultaneously and equally. Likewise, when there is no external force applied to the control bar by a user or a portable electronic device 14, the spring force of the springs 62 acting on the latches 50, 54 will cause the control bar 74 to be moved to and remain in the downward position, with the latches 50, 54 in their latched positions.

Figure 1:
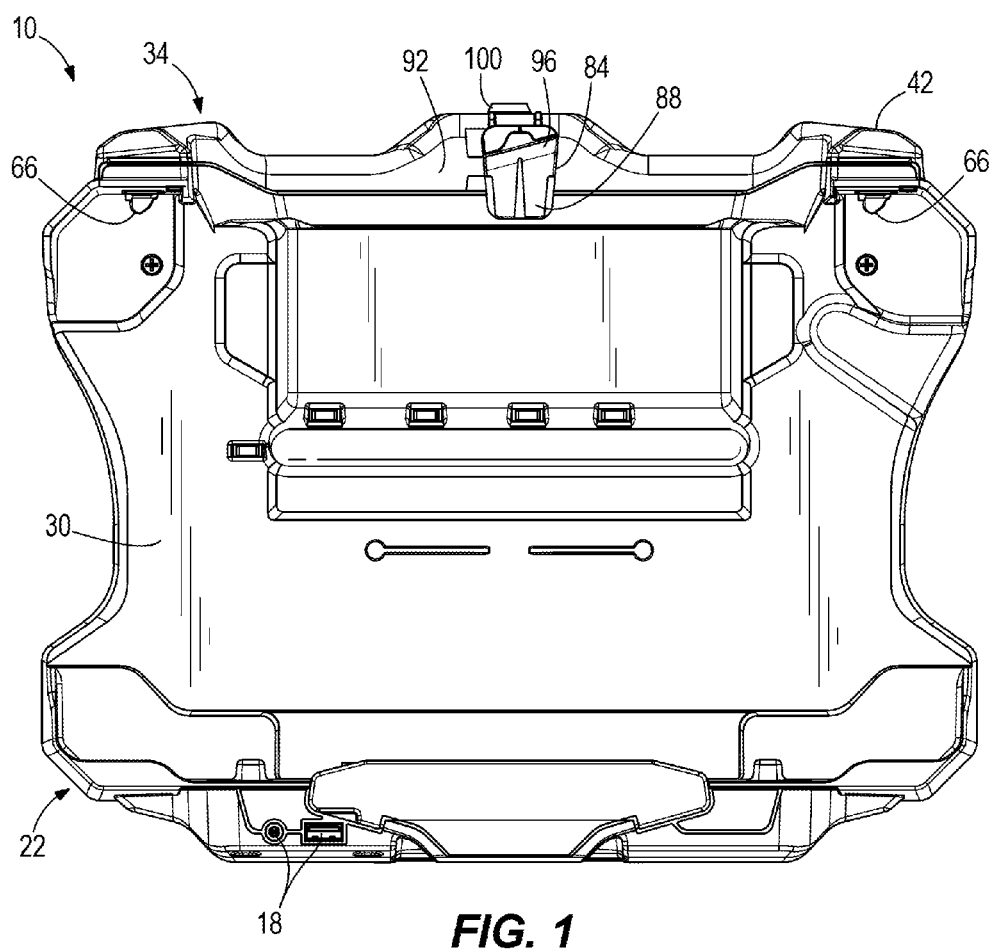
FIG. 1 is a front view of a docking station for an electronic device embodying the invention.
Figure 2:
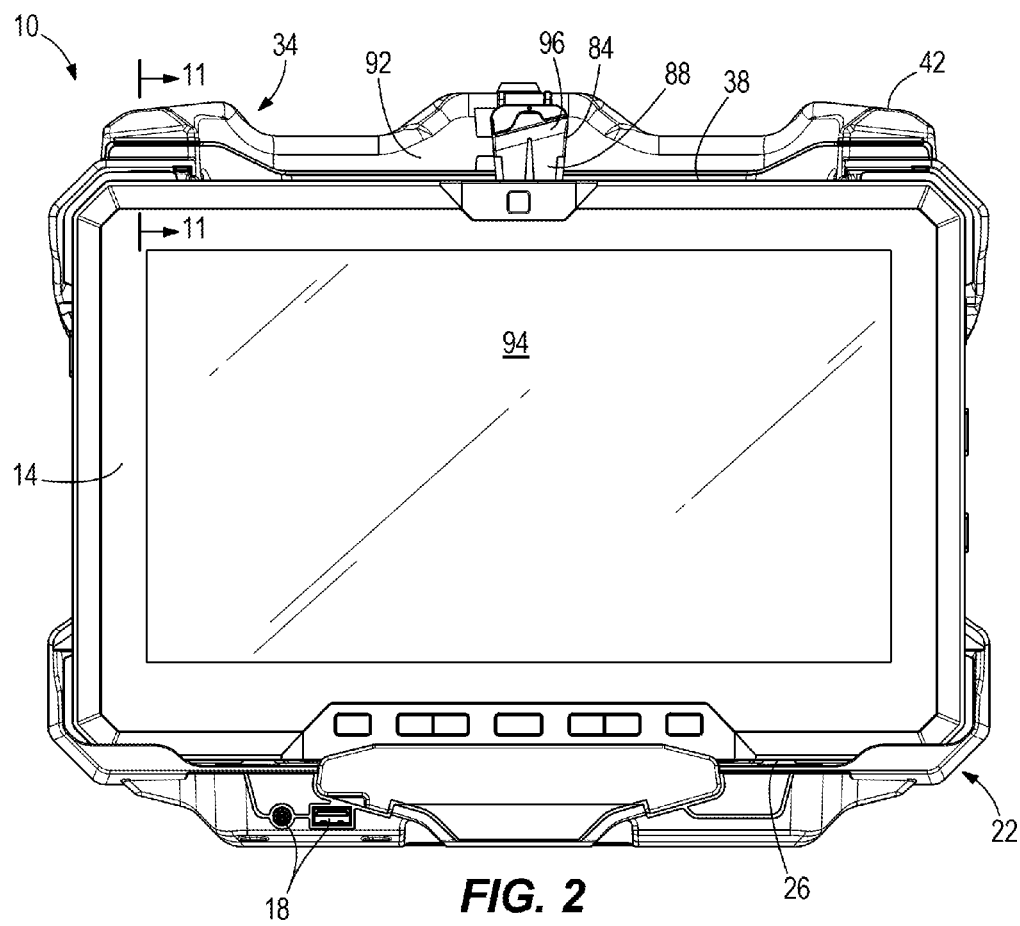
FIG. 2 is a front view of the docking station of FIG. 1, illustrated with an electronic device docked therein.

The latching system 46 further includes an actuator 84 coupled to the control bar 74. In the illustrated embodiment, the actuator 84 is coupled to the control bar 74 near the center of the control bar 74 and as such, near the center of the latching portion 34 of the docking station 10. With reference to FIGS. 1 and 2, the actuator 84 has a first surface portion 88 that is generally parallel to a front face 92 of the housing 42 (and to a front surface 94 of the portable electronic device 14), and has a second surface portion 96 that is angled or curved relative to (e.g., away from) the first surface portion 88 to enable a user to provide an upward force to the actuator 84 (e.g., by using a single thumb or finger) to lift the control bar 74 for unlatching the portable electronic device 14. The actuator 84 can be integrally formed as one piece with the control bar 74, or can be a separate piece connected to the control bar 74. As best shown in FIG. 1, only the actuator 84 and the distal ends 66 of the latches 50, 54 are visible outside the housing 42 of the docking station 10. As shown in FIG. 2, when the portable electronic device 14 is docked in the docking station 10, the distal ends 66 are received in the respective apertures 70 of the portable electronic device 14 such that only the actuator 84 is visible outside the housing 42. In alternative embodiments, the distal ends 66 of the latches 50, 54 could be configured to engage other portions of the portable electronic device 14, including the front surface 94 adjacent the upper edge 38, instead of apertures in the upper edge 38, to latch and secure the portable electronic device 14 in the docking station 10.

Figure 16A:
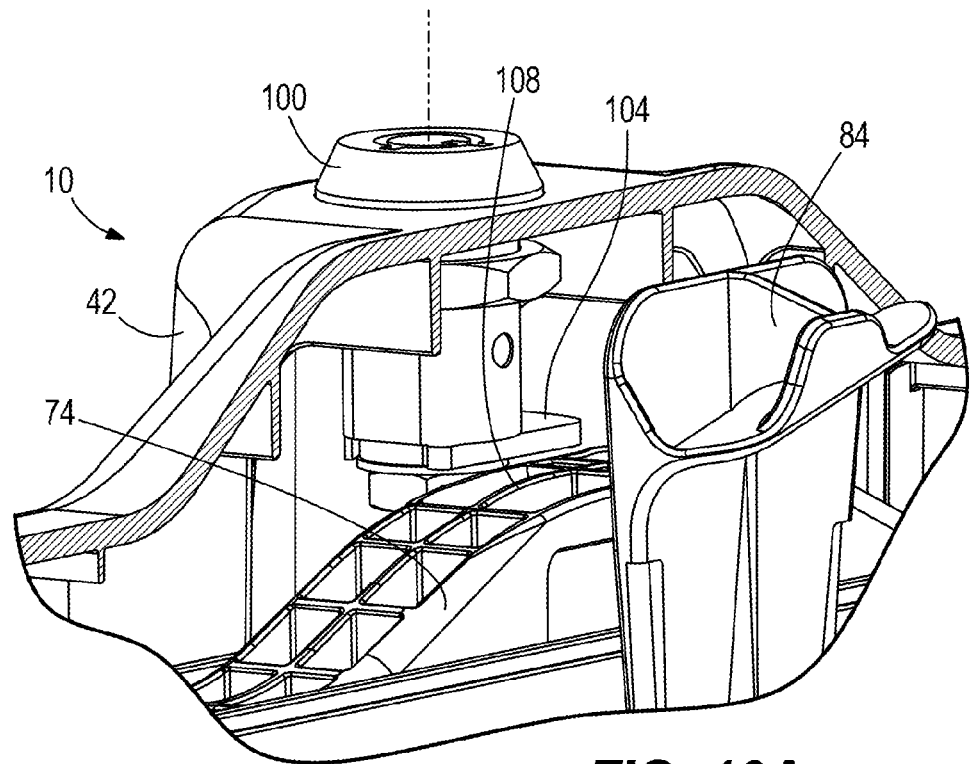
FIG. 16A illustrates a lock in an unlocked state to allow movement of the latching system.
Figure 16B:
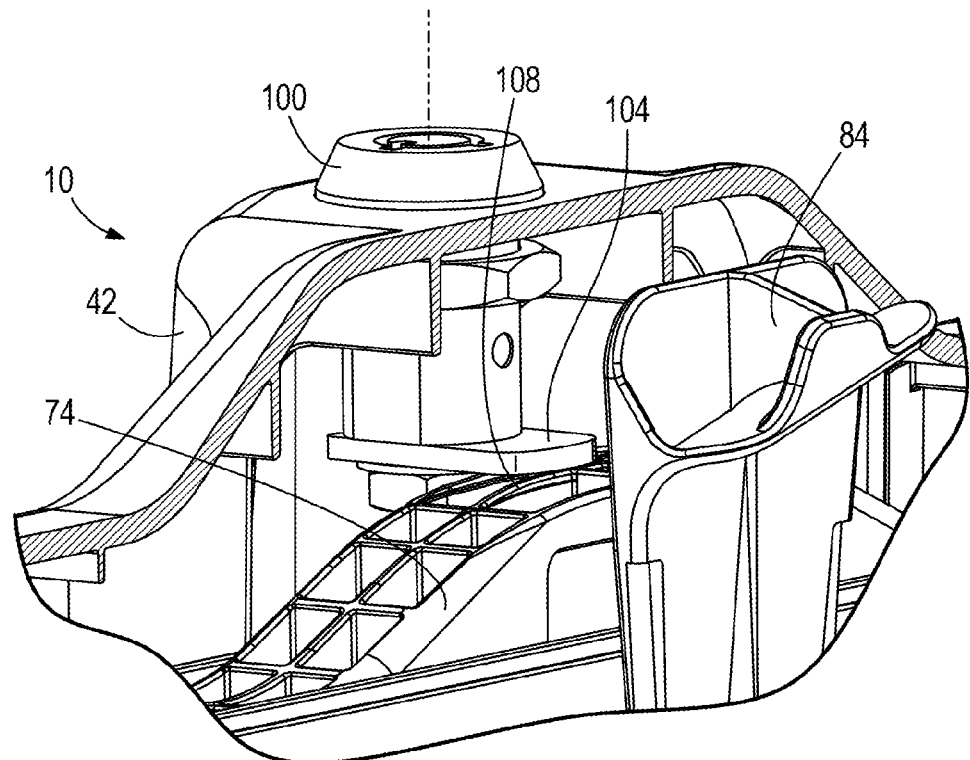
FIG. 16B illustrates a lock in a locked state to prevent movement of the latching system.

In some embodiments, and as best shown in FIGS. 16A and 16B, the latching system 46 can further include a lock 100 supported by the housing 42 to interact with the control bar 74 to selectively prevent or allow upward movement of the control bar 74. Specifically, when the lock 100 is in the locked state, an engaging portion 104 of the lock 100 is positioned to prevent the control bar 74 from moving in an upward direction, thereby preventing the movement of the latches 50, 54 to the unlatched position. Alternatively, when the lock 100 is in the unlocked state, the engaging portion 104 of the lock 100 is positioned to allow upward movement of the control bar 74 so that the latches 50, 54 are free to rotate to the unlatched position. Any suitable lock configuration (e.g., a keyed cylinder lock) can be used to interface with the control bar 74. In the illustrated embodiment, the turning of a key in the lock 100 rotates the engaging portion or tab 104 to a position in which an engaging portion or upper surface 108 of the control bar 74 abuts the tab 104 of the lock 100 to prevent upward movement of the control bar 74. In other embodiments, the engaging portion of the lock 104 could be moved linearly instead of rotationally to abut the control bar 74. In yet other embodiments, the lock 100 may interact with the actuator 84 or the latches 50, 54 to selectively lock the latching system 46.

The operation of the latching system 46 will now be described with reference to FIGS. 11-15A. To insert the portable electronic device 14 into the docking station 10, a user first positions the lower edge 26 of the portable electronic device 14 into the cradle portion 22. This insertion connects the portable electronic device 14 to the electrical connector 16. In other embodiments, the cradle portion 22 need not include an electrical connector, such as in situations where the portable electronic device 14 does not include an electrical connector, or is instead just held or supported in the docking station 10.

Figure 11:
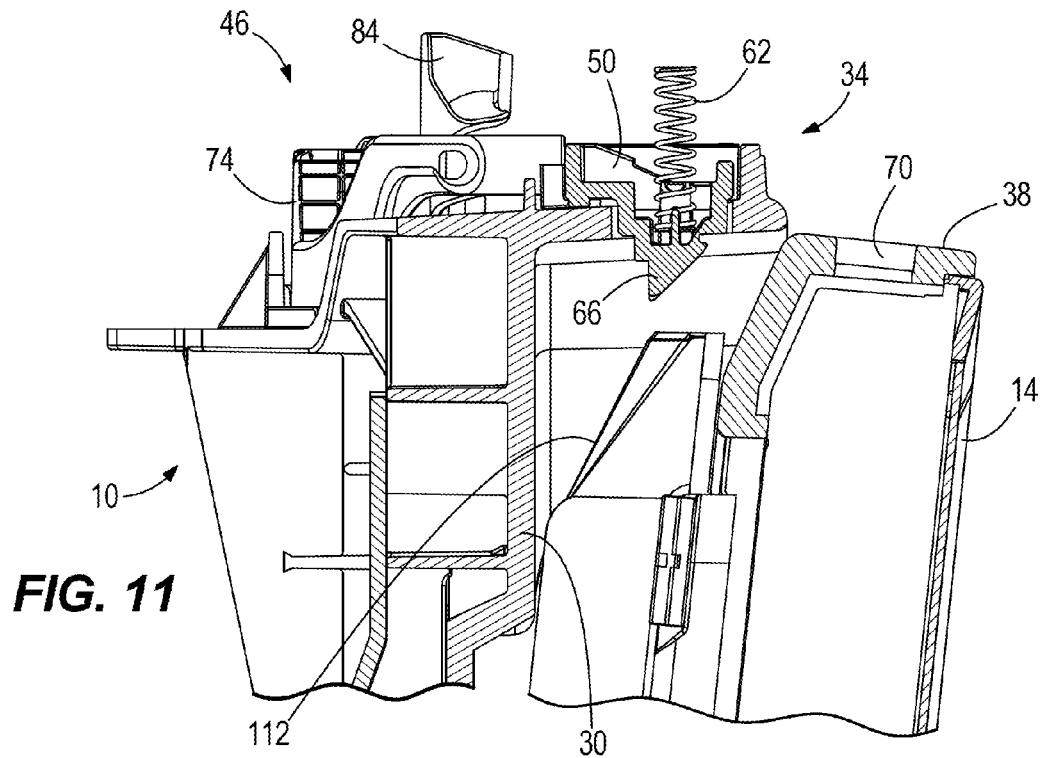
FIGS. 11-14 are partial section views, with a portion of the housing removed, illustrating the sequence of installing the electronic device into the docking station.
Figure 12:
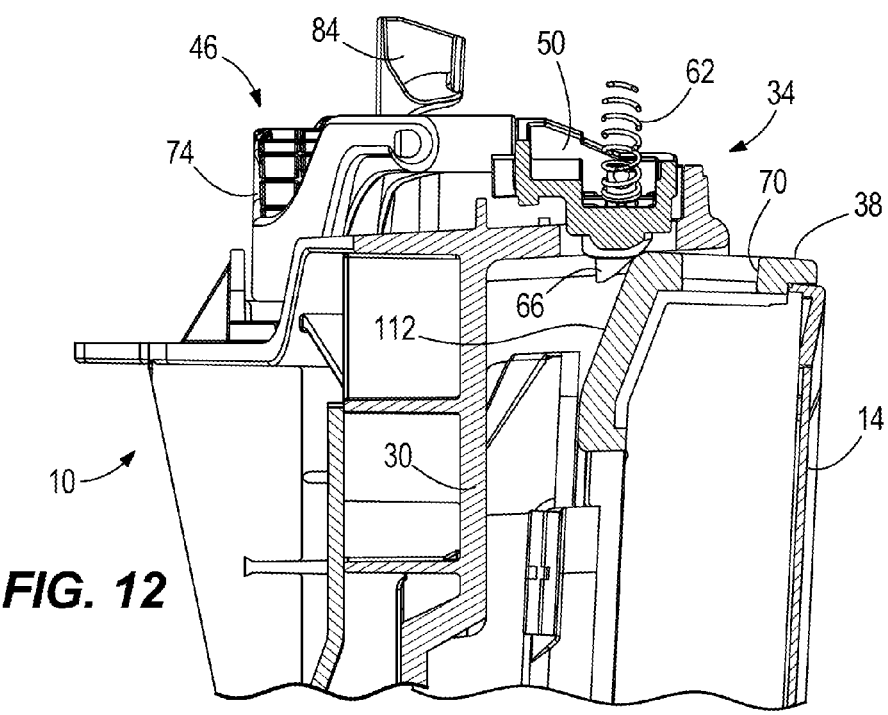

Next, the user pivots the upper edge 38 of the portable electronic device 14 toward the latching portion 34 such that a rear surface 112 of the portable electronic device 14 moves toward the body portion 30 of the docking station 10. FIG. 11 illustrates an initial position of the upper edge 38 of the portable electronic device 14 after the lower edge 26 has been positioned in the cradle portion 22 and prior to engagement of the upper edge 38 with the distal ends 66 of the latches 50, 54. In FIG. 12, as the user continues to rotate the upper edge 38 toward the latching portion 34, the rear surface 112 and/or the upper edge 38 of the portable electronic device 14 contacts the distal ends 66 of the latches 50, 54 substantially simultaneously.

Figure 8:
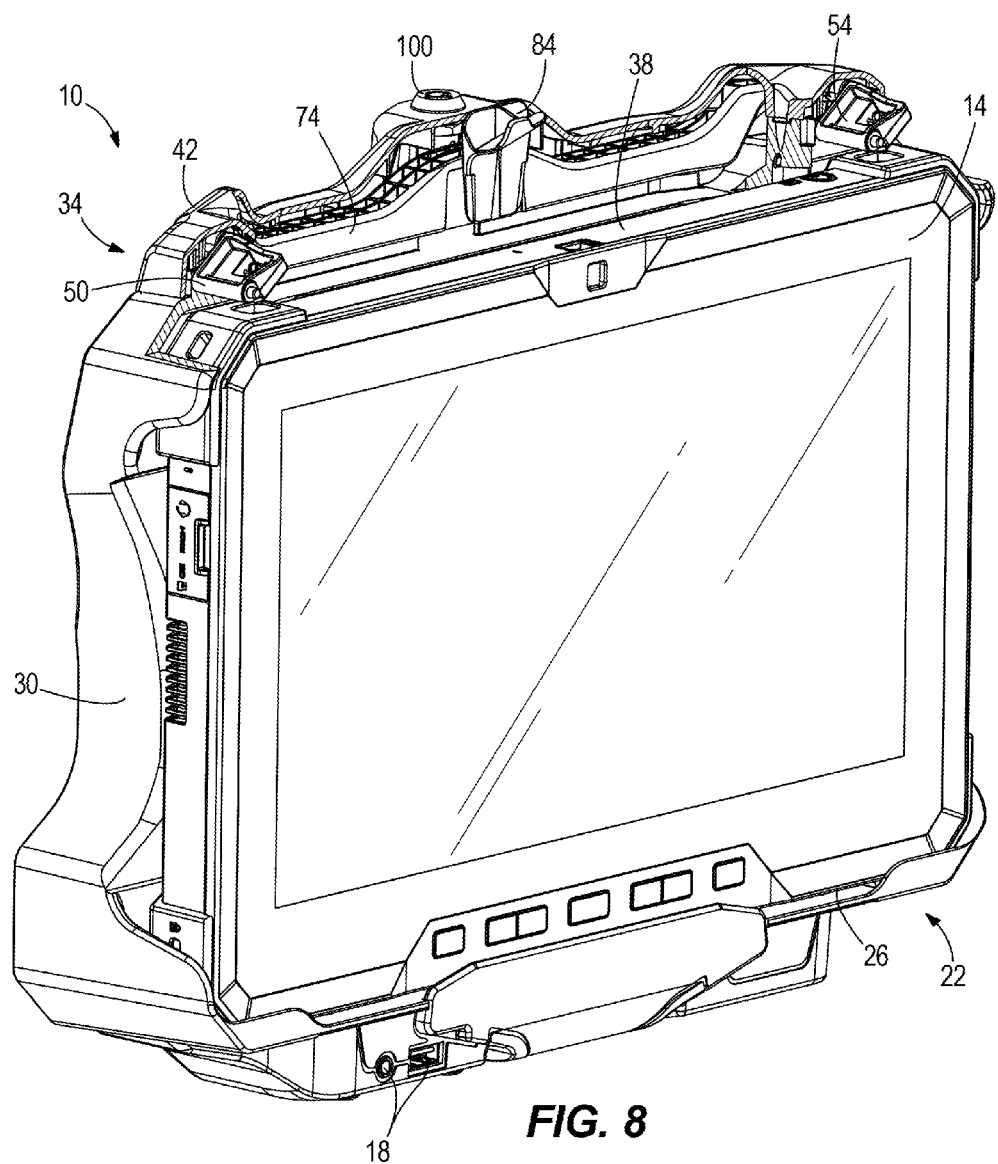
FIG. 8 is a perspective view of the docking station, partially broken away, illustrating the latching system in the unlatched position to allow removal of the electronic device.
Figure 9:
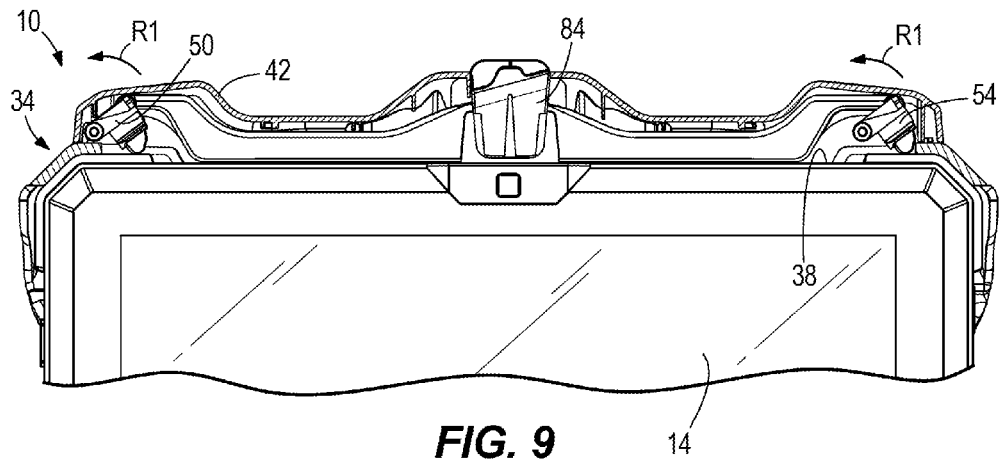
FIG. 9 is a partial front view of FIG. 8 illustrating the latching system in the unlatched position to allow removal of the electronic device.
Figure 10:
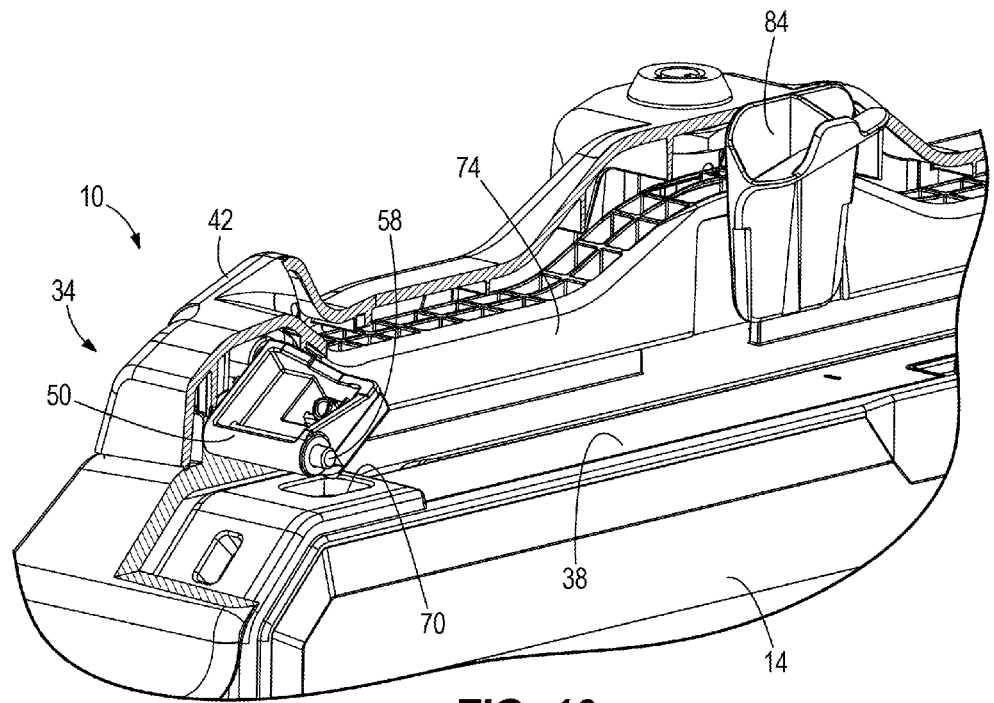
FIG. 10 is an enlarged partial perspective view of the arrangement of FIG. 8.
Figure 13:
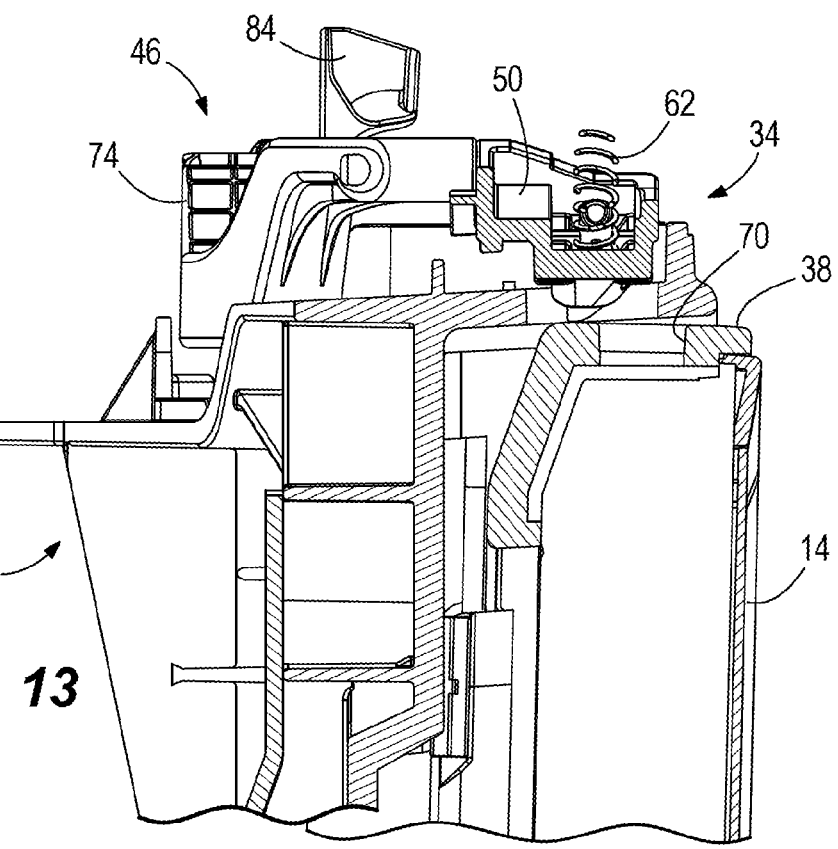
Figure 14:
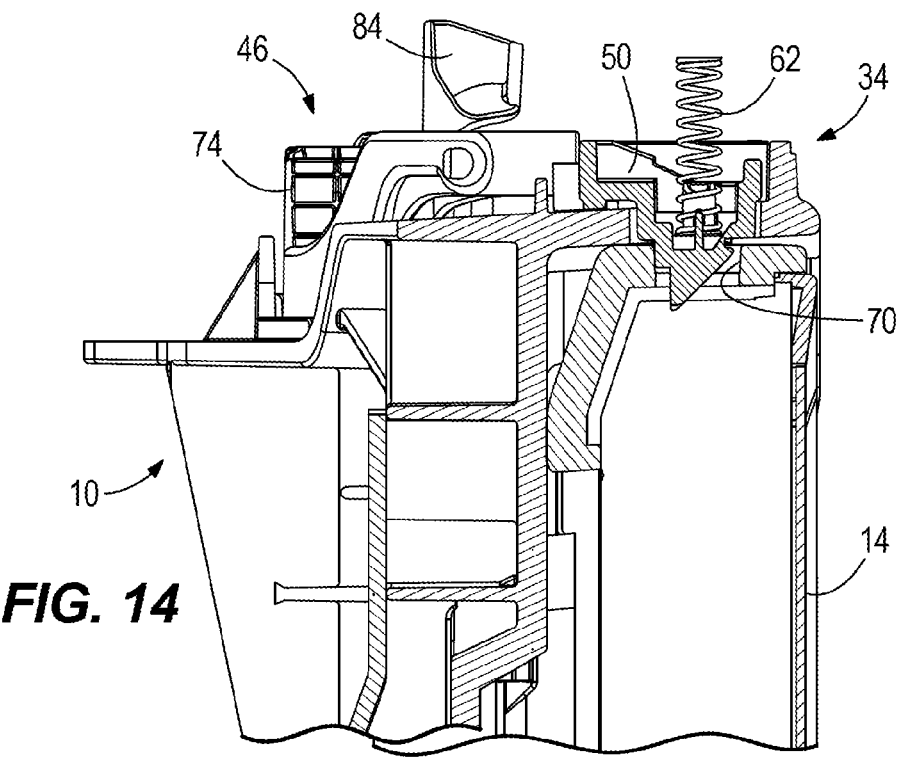
Figure 15A:
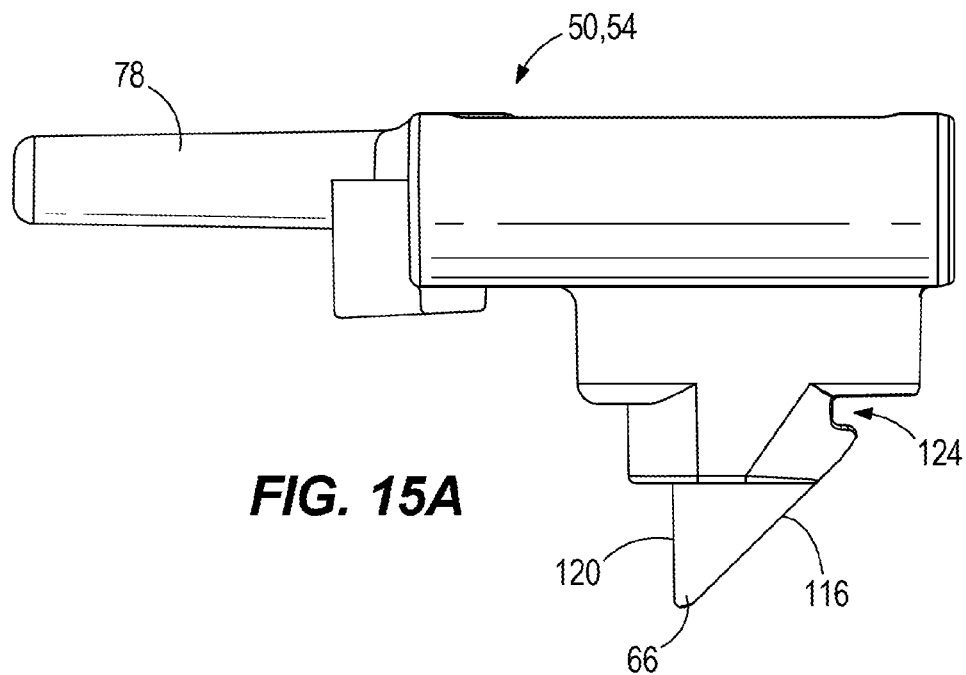
FIG. 15A is a side view of a latch of the latching system.
Figure 15B:
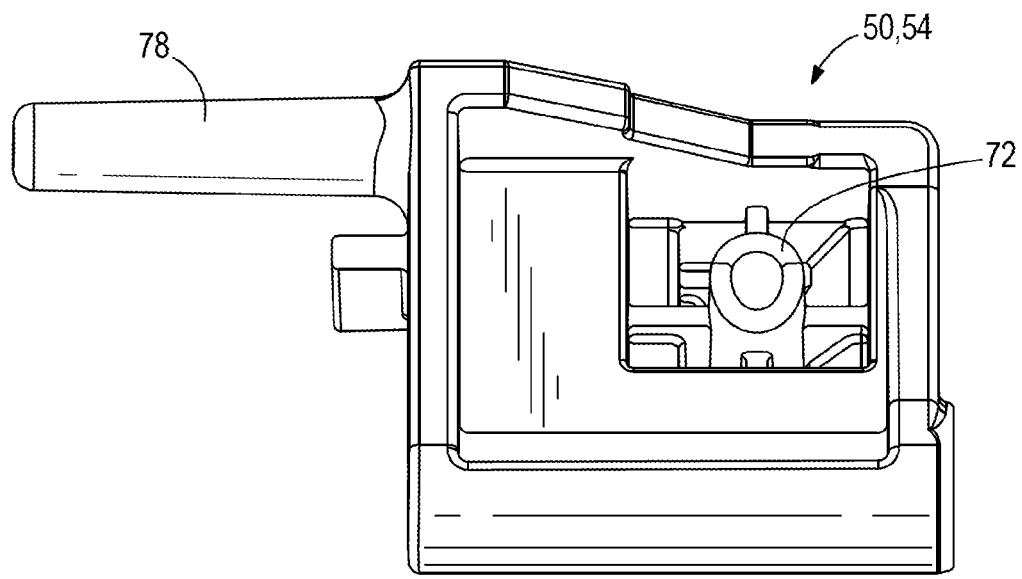
FIG. 15B is a top perspective view of a latch of the latching system.

FIG. 15A illustrates the latches 50, 54 (both latches 50, 54 are identical so only one is shown). The distal end 66 of each latch 50, 54 includes a ramped surface 116 that is contacted by the rear surface 112 and/or the upper edge 38 of the portable electronic device 14 as the device 14 is being rotated toward the latching portion 34. These ramped surfaces 116 enable the latches 50, 54 to move or rotate toward the unlatched position (counter clockwise as shown in FIGS. 8-10—see arrows R1 in FIG. 9) via a camming action as the portable electronic device 14 is rotated toward the docking station 10. The force exerted by the user on the portable electronic device 14 against the ramped surfaces 116 overcomes the bias of the springs 62 to enable rotation of the latches 50, 54 (and the resulting lifting of the control bar 74 and the actuation portion 84). The rotation of the latches 50, 54 occurs in a plane perpendicular to the direction of force applied by the portable electronic device 14 to the ramped surfaces 116. In other words, the ramped surfaces 116 convert the directional force applied by the portable electronic device 14 into rotational motion of the latches 50, 54 in a plane perpendicular to the direction of the movement of the portable electronic device 14 toward the latching portion 34. FIG. 13 illustrates how the distal ends 66 of the latches 50, 54 will rotate toward the unlatched position to be in engagement with the upper edge 38 of the portable electronic device 14. As the user continues to rotate the portable electronic device 14 toward the latching portion 34, the distal ends 66 will slide along the upper edge 38 until they engage and drop into the respective apertures 70 formed in the upper edge 38, as shown in FIG. 14. The bias of the springs 62 will urge the distal ends 66 downwardly, causing them to rotate counter-clockwise (see arrows R2 in FIG. 6) into the apertures 70 as the rear surface 112 of the portable electronic device 14 engages the body portion 30 so that the portable electronic device 14 is latched in the docked position. In the position illustrated in FIG. 14, the portable electronic device 14 is docked and latched with the distal ends 66 being fully received in the apertures 70. By virtue of the ramped surfaces 116 and the bias of the springs 62, it can be understood how the latching system 46 operates automatically, that is, without any separate actuation by the user, when the portable electronic device 14 is installed into the docking station 10. The latching system 46 can be referred to as a "dual slam latch" in that the engagement or "slamming" of the portable electronic device 14 into the two latches 50, 54 will automatically cause the latches 50, 54 to secure and latch the portable electronic device 14 in the docking station 10.

As shown in FIG. 15A, the surface 120 of the distal ends 66 opposite the ramped surface 116 is not ramped, but rather is generally vertical so that attempts to rotate or pull the upper edge 38 of the portable electronic device 14 away from the latching portion 34 will not cause any camming action or other movement capable of rotating the latches 50, 54 to the unlatched position. If the user then desires to lock the portable electronic device 14 in the docking station 10, the lock 100 can be locked to prevent upward movement of the control bar 74, thereby preventing the latches 50, 54 from moving or rotating to the unlatched position.

Figure 21:
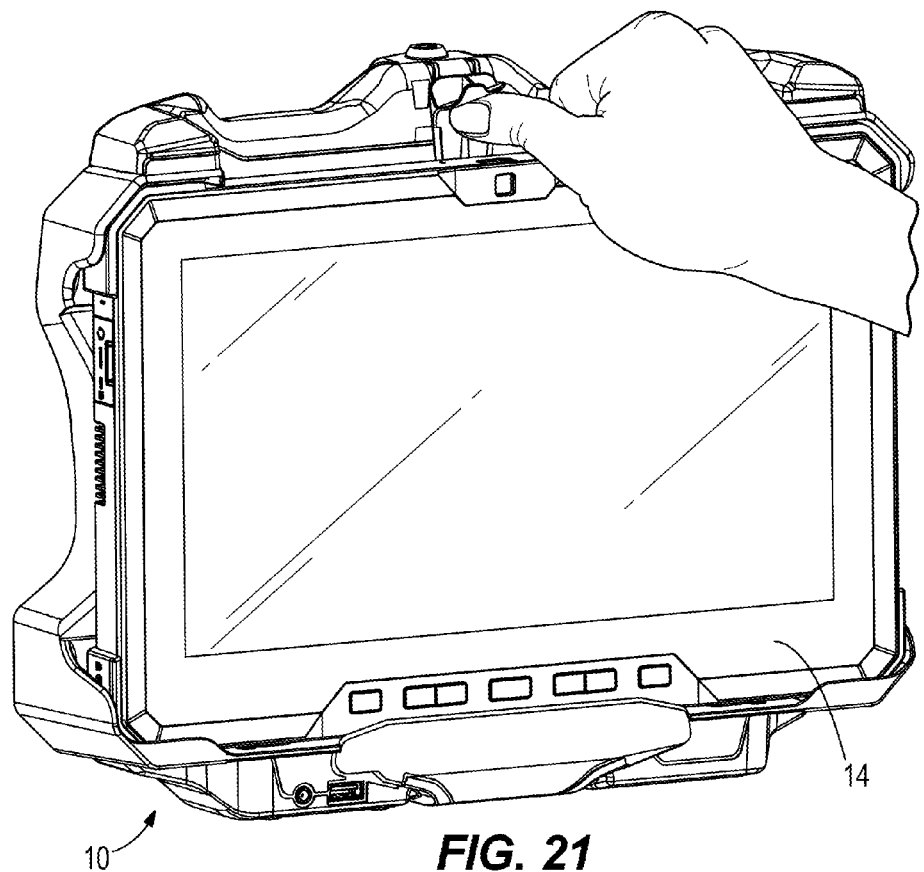
FIGS. 21 and 22 illustrate one-handed operation by a user of the docking station to remove a portable electronic device.
Figure 22:
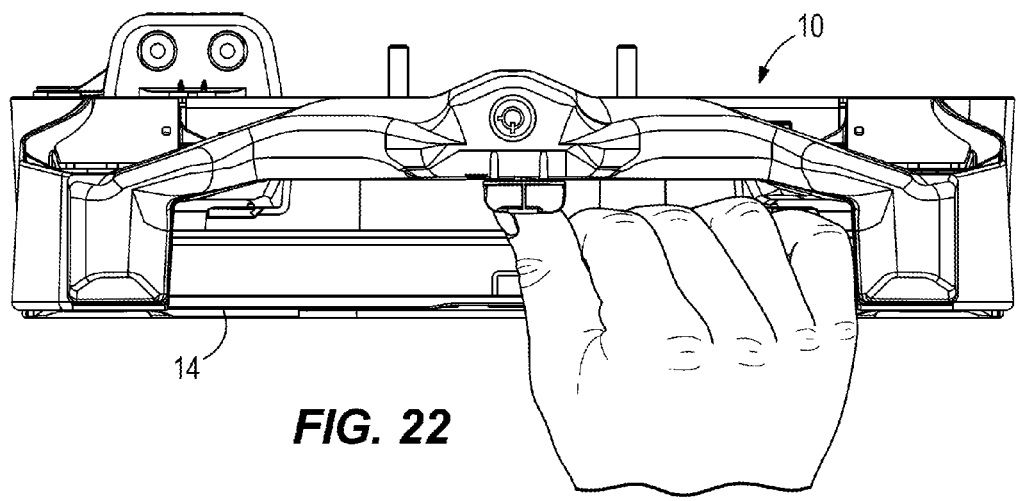

To remove the portable electronic device 14 from the docking station 10, a user first unlocks the lock 100 (if it was locked). With the lock 100 unlocked, the control bar 74 is free to be moved in the upward direction. This can be accomplished by the user with a single thumb or finger exerting an upward force on the actuator 84, and preferably by pressing upwardly on the second surface portion 96 of the actuator 84. The pins 78 are received in the apertures 76, 80 of the control bar 74 so that lifting the control bar 74 simultaneously lifts the two spaced-apart latches 50, 54 upwardly against the bias of the springs 62, so that the latches 50, 54 move or rotate about pivot pins 58 together and simultaneously to the unlatched position, as shown in FIGS. 8-10. The distal ends 66 are thereby removed from the apertures 70 so that the upper edge 38 of the portable electronic device 14 can be rotated away from the latching portion 34. A user will be able to lift the actuator 84 and grasp and rotate the portable electronic device 14 with a single hand for easy removal of the portable electronic device 14 from the docking station 10 (see FIGS. 21 and 22). Once the upper edge 38 is clear of the distal ends 66 and the remainder of the housing 42 at the latching portion 34, the user can stop applying upward force to the actuator 84 and the lower edge 26 of the portable electronic device 14 can be removed from the cradle portion 22 to free the portable electronic device 14.

Figure 17:
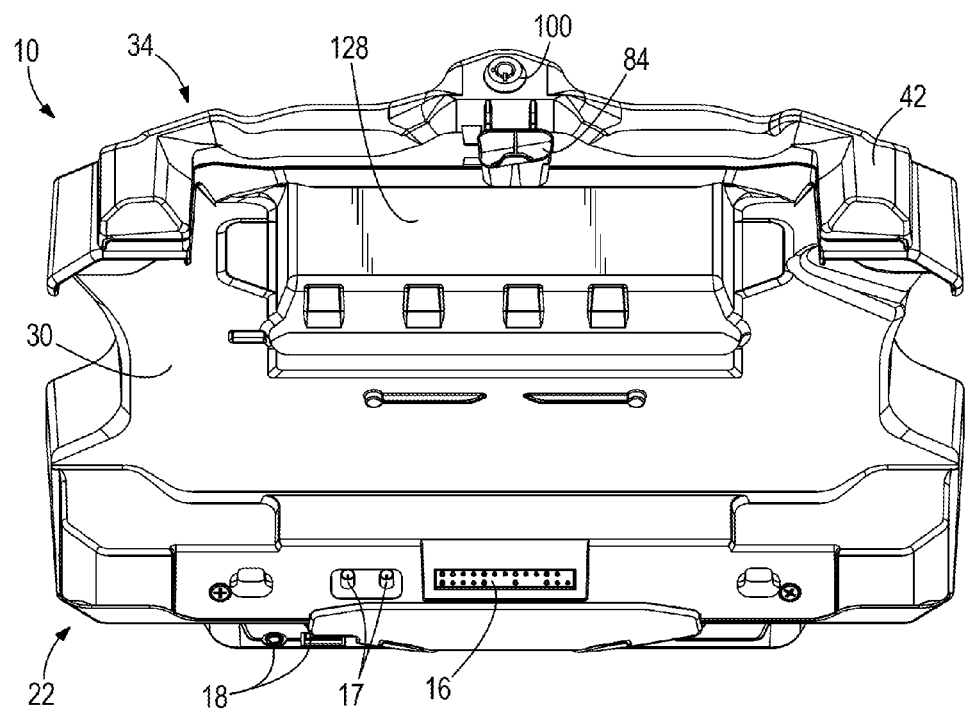
FIG. 17 is a top perspective view of the docking station of FIG. 1.
Figure 18:
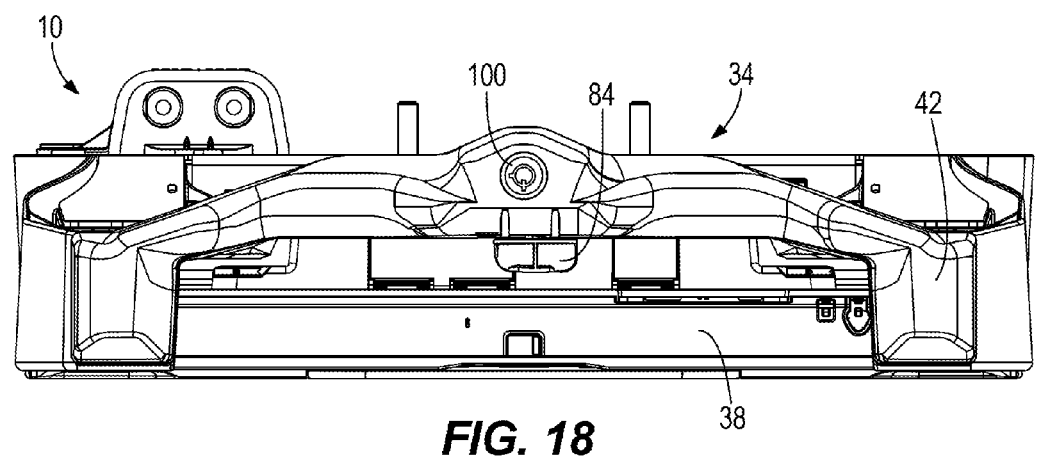
FIG. 18 is a top view of the docking station of FIG. 1, illustrated with a portable electronic device docked therein.
Figure 19:
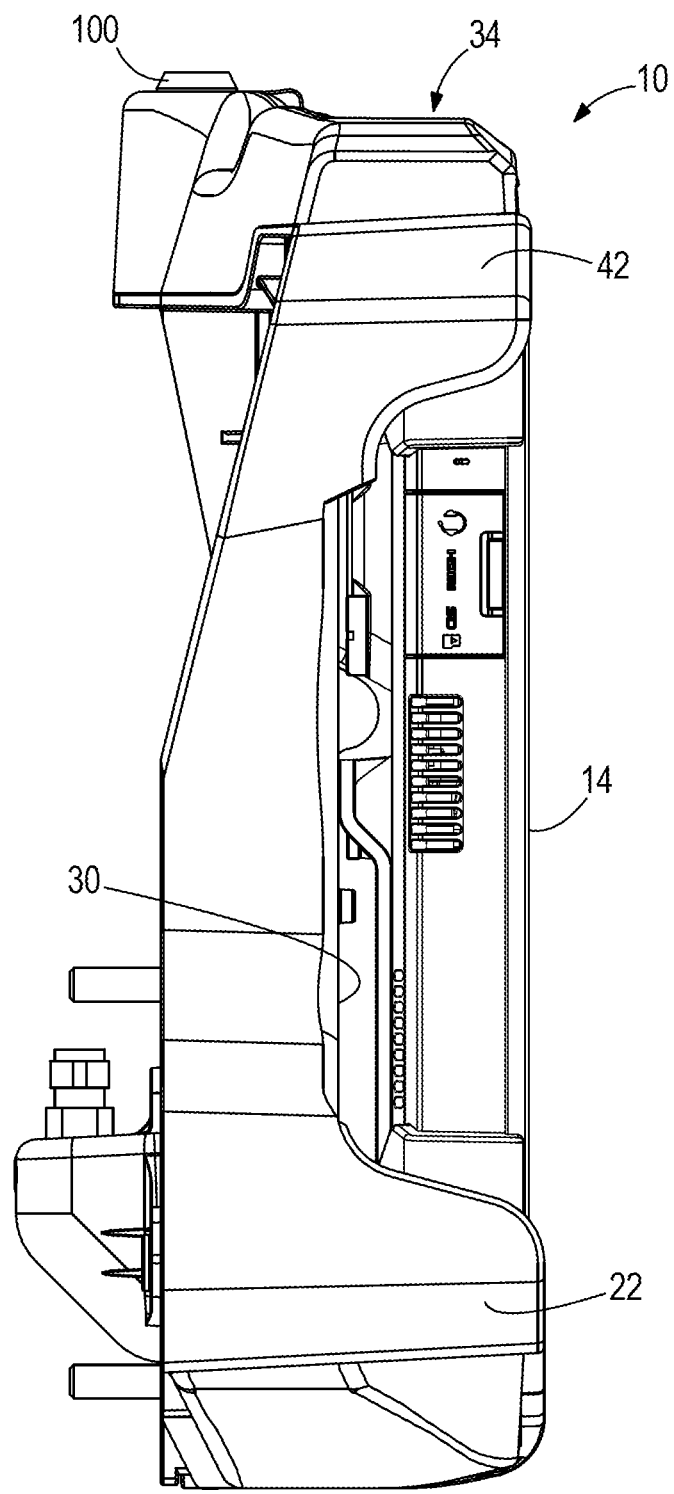
FIG. 19 is a side view of the docking station of FIG. 1, illustrated with a portable electronic device docked therein.

As best shown in FIGS. 17 and 18, it can be seen that the portions of the housing 42 that contain the latches 50, 54 extend outwardly in a direction perpendicular to and away from the body portion 30 further than the remainder of the housing 42 between the latches 50, 54. Therefore, the housing 42 at the latching portion 34 overhangs or covers the upper edge 38 of the portable electronic device 14 adjacent the two latches 50, 54, but does not overhang or cover the upper edge 38 of the portable electronic device 14 intermediate the two latches 50, 54 and especially adjacent the actuator 84. The user is then free to engage/grasp the upper edge 38 with his/her fingers while pressing the actuator 84 up with his thumb to release the portable electronic device 14 from the latching system 46 with a single hand (see FIGS. 21 and 22). As best shown in FIG. 17, the body portion 30 can also include a recessed portion 128 between the latches 50, 54 to provide clearance for the user's fingers. By virtue of the rigid control bar 74, and its unique engagement with the two latches 50, 54, the latching system 46 provides the added security offered by two, spaced-apart latches 50, 54 (with two spaced-apart points of securement for the portable electronic device 14), while still being easily operable with a single hand to unlatch and remove the portable electronic device 14.

Furthermore, by using two identical latches 50, 54 asymmetrically mounted so as to both rotate in the same direction (illustrated as counter-clockwise for latching and clockwise for unlatching), the simple yet effective mounting arrangement of the pins 78 and apertures 76, 80 can be used for the rigid control bar 74. Specifically, because the two latches 50, 54 will rotate in the same direction for unlatching (counterclockwise), the control bar 74 can be rigid and one piece, and the pins 78 can be fixed in the apertures 76, 80 without the need to account for any lateral change in spacing between the pins 78. Lifting of the control bar 74 will rotate the latches 50, 54 and there will be some arcuate/translational movement of the control bar 74 (in the direction of arrow R3 in FIG. 3) as the latches 50, 54 rotate, but the distance between the pins 78 will not change. In other words, the distance between the pins 78, and the respective first and second pivot points they define with the control bar 74, is constant or fixed. If the latches were symmetrically mounted to rotate in opposite directions for unlatching, two different latches would be needed. Furthermore, the distance between pins 78 would change during the rotation of the latches, thereby requiring some flexibility in the control bar or the interconnections between the control bar and the latches. While a more complicated and less stable linkage or slotting arrangement could be used, the illustrated embodiment offers a robust approach that minimizes the number of parts (and therefore tooling costs), while still providing the benefit of one-handed operation of a dual-latch system.

In the illustrated embodiment, the latches 50, 54 are equipped with an anti-theft or anti-tampering feature that protects against attempts to steal the portable electronic device 14 when locked in the docked state. As shown in FIG. 15A, at least one of the latches 50, 54 includes a slot or catch 124 located adjacent (e.g., just above) the ramped surface 116. If a person would attempt to insert a flat, hard object (e.g., a credit card) adjacent latches 50, 54 between the upper edge 38 of the portable electronic device 14 and a lower extremity of the housing 42 (see also FIG. 14), in an attempt to access the ramped surfaces 116 and force the camming action upon the latches 50, 54 when the control bar 74 is engaged by lock 100, the flat, hard object would instead be directed to enter the slot or catch 124, thereby preventing the object from engaging the ramped surface 116 and forcing the unauthorized movement or rotation of the latches 50, 54.

Various features and advantages of the invention are set forth in the following claims.

What is claimed is:

1. A docking station for a portable electronic device, the docking station comprising:
   a cradle portion for supporting a first edge of the portable electronic device;
   a body portion extending away from the cradle portion; and
   a latching portion coupled to the body portion for securing a second edge of the portable electronic device when the portable electronic device is supported in the docking station, the latching portion including,
      a first latch movable relative to the body portion in a plane between a latched position and an unlatched position;
      a second latch spaced from the first latch and movable relative to the body portion in the plane between a latched position and an unlatched position; and
      a control bar coupled to each of the first and second latches such that movement of the control bar by a user simultaneously moves both the first and second latches to the unlatched positions.

2. The docking station of claim 1, wherein the first latch is adjacent a first corner of the docking station and the second latch is adjacent a second corner of the docking station, and wherein the control bar is a rigid member extending between the first and second latches.

3. The docking station of claim 1, wherein each of the first and second latches is pivotally coupled to the docking station via a respective pivot pin, and wherein the first and second latches both rotate about their respective pivot pins between the latched and unlatched positions.

4. The docking station of claim 3, wherein the first and second latches rotate in the same direction when moving from the latched position to the unlatched position.

5. The docking station of claim 1, wherein the control bar is coupled to the first latch at a first end of the control bar by a first pin, and wherein the control bar is coupled to the second latch at a second end of the control bar by a second pin.

6. The docking station of claim 5, wherein the control bar includes a first aperture at the first end of the control bar that receives the first pin, the first pin being integrally formed with the first latch, and wherein the control bar includes a second aperture at the second end of the control bar that receives the second pin, the second pin being integrally formed with the second latch.

7. The docking station of claim 1, wherein the latching portion further includes at least one spring biasing the first and second latches toward the latched position.

8. The docking station of claim 1, wherein each of the first and second latches includes a ramped surface configured such that engagement of the ramped surfaces by a portable electronic device being inserted into the docking station moves the first and second latches toward the unlatched position.

9. The docking station of claim 8, wherein engagement of the ramped surfaces by a portable electronic device being inserted into the docking station moves the first and second latches toward the unlatched position and also causes movement of the control bar.

10. The docking station of claim 8, wherein each of the first and second latches is biased toward the latched position by a spring such that once the portable electronic device is fully inserted into the docking station, the first and second latches move to the latched position via the spring bias.

11. The docking station of claim 8, wherein at least one of the first or second latches further includes a slot adjacent the ramped surface, the slot sized and configured to receive a device.

12. The docking station of claim 1, wherein the latching portion further includes an actuator coupled to the control bar, the actuator configured to be operated by a user to move the control bar.

13. The docking station of claim 12, wherein the actuator is positioned between the first and second latches.

14. The docking station of claim 13, wherein the actuator is positioned relative to the body portion so that the actuator can be operated and the upper edge of the portable electronic device can be engaged at the same time with a single hand of the user to enable undocking of the portable electronic device from the docking station with a single hand.

15. The docking station of claim 12, wherein the actuator is integrally formed with the control bar.

16. The docking station of claim 1, further comprising a lock operable to selectively prevent or allow movement of the first and second latches.

17. The docking station of claim 16, wherein the lock cooperates with the control bar to selectively prevent or allow movement of the control bar.

18. The docking station of claim 1, wherein each of the first and second latches includes a distal end sized and configured to be received in a respective aperture formed in a portion of the portable electronic device.

19. The docking station of claim 1, wherein portions of a housing that contain the first and second latches extend outwardly in a direction perpendicular to and away from the body portion further than a remainder of the housing between the first and second latches such that the housing overhangs the upper edge of a docked portable electronic device adjacent the two latches but does not overhang the upper edge of the docked portable electronic device intermediate the two latches.

20. A docking station for a portable electronic device, the docking station comprising:
- a cradle portion for supporting a first edge of the portable electronic device;
- a body portion extending away from the cradle portion; and
- a latching portion coupled to the body portion for securing a second edge of the portable electronic device when the portable electronic device is supported in the docking station, the latching portion including,
  - a housing;
  - a first latch movable relative to the body portion in a plane between a latched position and an unlatched position;
  - a second latch spaced from the first latch and movable relative to the body portion in the plane between a latched position and an unlatched position; and
  - a control bar coupled to each of the first and second latches such that movement of the control bar by a user simultaneously moves both the first and second latches to the unlatched positions;
- wherein each of the first and second latches is pivotally coupled to the housing at a respective pivot point, and wherein the first and second latches both rotate in the same direction about their respective pivot points between the latched and unlatched positions.

21. A docking station for a portable electronic device, the docking station comprising:
- a cradle portion for supporting a first edge of the portable electronic device;
- a body portion extending away from the cradle portion; and
- a latching portion coupled to the body portion for securing a second edge of the portable electronic device when the portable electronic device is supported in the docking station, the latching portion including,
  - a first latch movable relative to the body portion in a plane between a latched position and an unlatched position;
  - a second latch spaced from the first latch and movable relative to the body portion in the plane between a latched position and an unlatched position; and
  - a control bar coupled to each of the first and second latches such that movement of the control bar by a user simultaneously moves both the first and second latches to the unlatched positions;
- wherein the control bar is coupled to the first latch at a first pivot point, and wherein the control bar is coupled to the second latch at a second pivot point; and
- wherein a distance between the first and second pivot points is constant during movement of the first and second latches between the latched and unlatched positions.

* * * * *